United States Patent [19]

Sakita

[11] Patent Number: 5,092,345
[45] Date of Patent: Mar. 3, 1992

[54] UTERINE CELL SAMPLER

[75] Inventor: Hirofumi Sakita, Tokyo, Japan

[73] Assignee: Anne Company Limited, Isehara, Japan

[21] Appl. No.: 408,490

[22] PCT Filed: Jan. 6, 1989

[86] PCT No.: PCT/JP89/00004
§ 371 Date: Mar. 16, 1990
§ 102(e) Date: Mar. 16, 1990

[87] PCT Pub. No.: WO89/06110
PCT Pub. Date: Jul. 13, 1989

[30] Foreign Application Priority Data

Jan. 11, 1988 [JP] Japan .................. 63-3552

[51] Int. Cl.$^5$ .............................................. A61B 10/00
[52] U.S. Cl. .............................................. 128/757
[58] Field of Search ................ 128/749, 751, 757, 759

[56] References Cited

U.S. PATENT DOCUMENTS

| 2,767,703 | 10/1956 | Nieburgs | 128/749 |
| 3,491,747 | 1/1970 | Robinson | 128/757 |
| 3,800,781 | 4/1974 | Zalucki | 128/749 |
| 4,338,952 | 7/1982 | Augros | 128/751 |
| 4,378,811 | 4/1983 | Levitan | 128/757 |

FOREIGN PATENT DOCUMENTS 55-99243 7/1980 Japan.
58-73208 5/1983 Japan.
63-135611 9/1988 Japan.
63-135612 9/1988 Japan.

Primary Examiner—Max Hindenburg
Attorney, Agent, or Firm—Oblon, Spivak, McClelland, Maier & Neustadt

[57] ABSTRACT

Described herein is a cell sampler particularly suitable for sampling cells from the uterine endometrium as specimens in cytodiagnosis for uterine cancer, especially, for carcinoma corporis, the sampler including a handle slidably and rotatably inserted in a tube and a scraper portion in the form of a flexible loop with scraper blades for scraping sample cells. The scraper portion is protrudably retractable into the tube by sliding movements of the handle, and capable of sampling cells from entire regions of the endometrium in a safe and reliable manner.

5 Claims, 4 Drawing Sheets

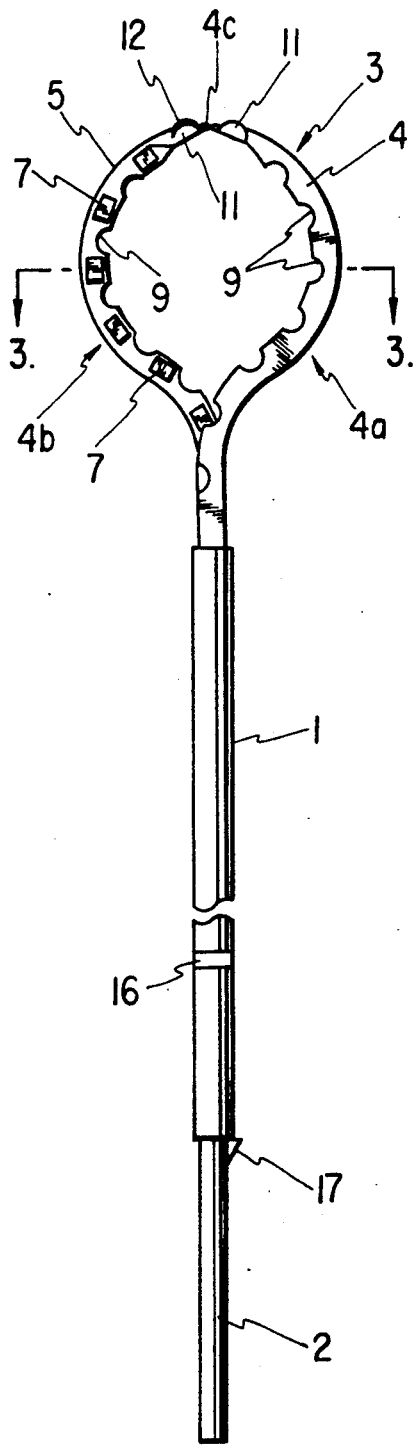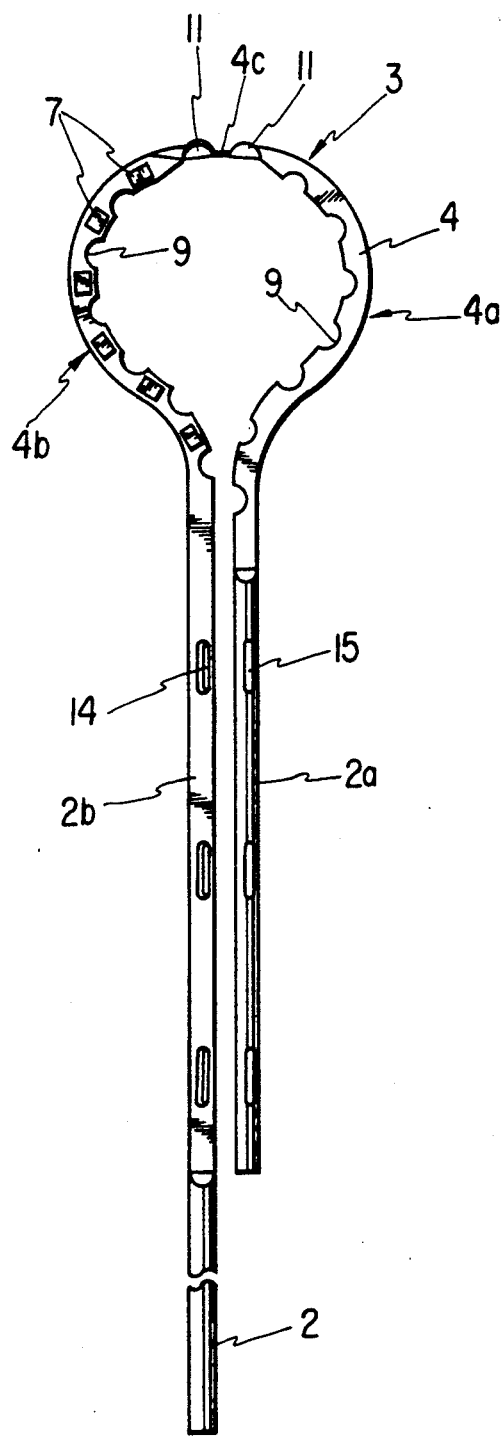

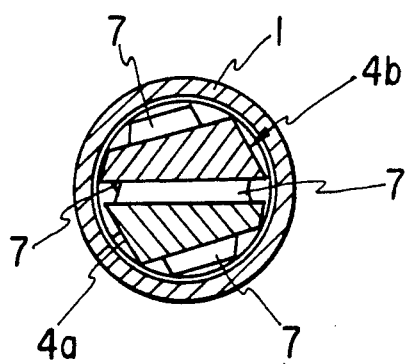
FIG.9
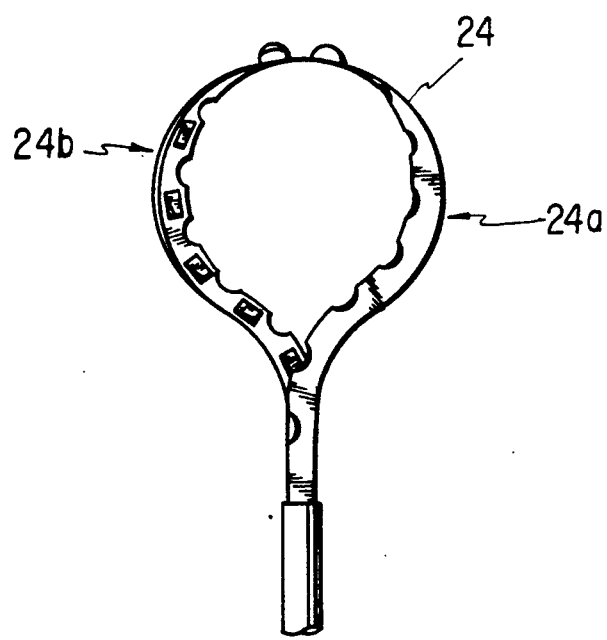
FIG.10
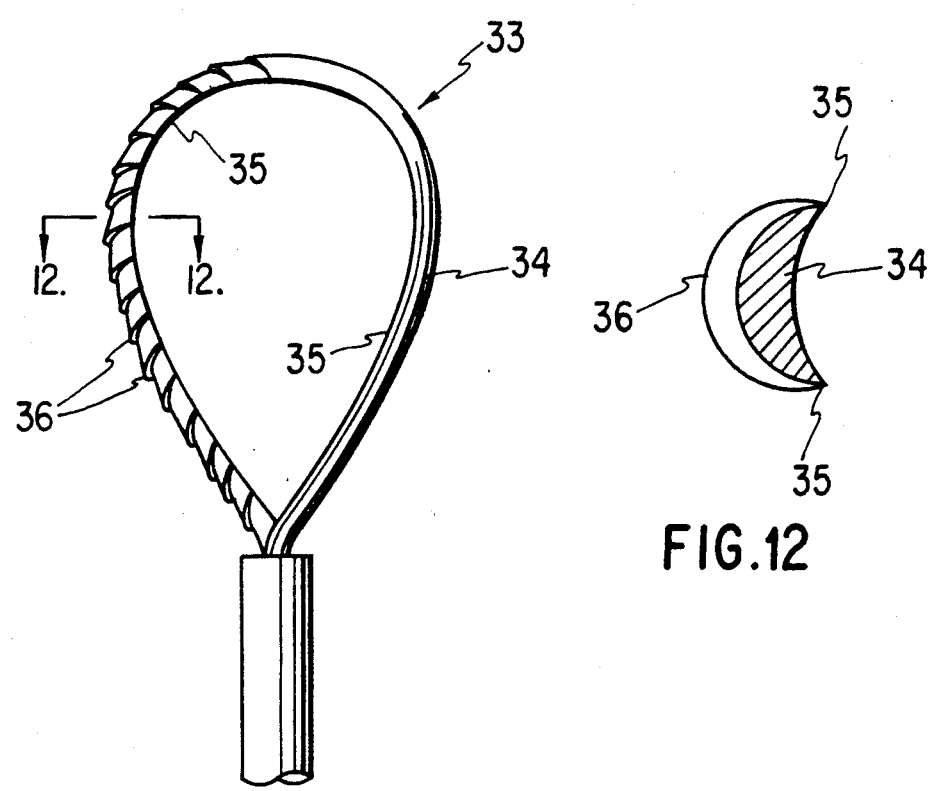
FIG.11
FIG.12

UTERINE CELL SAMPLER

BACKGROUND OF THE INVENTION

1. Field of the Invention

This invention relates to a cell sampler to be used for sampling cells from the endometrium as a specimen to be used in cytodiagnosis for uterine cancer, particularly in cytodiagnosis for carcinoma corporis.

2. Description of the Prior Art

Recently the rate of uterine cancer infection has been on a gradual increase. As well known in the art, the sooner therapy is given, the higher becomes the possibility of complete healing from uterine cancer. Therefore, it is desirable to find a uterine cancer in an early stage by periodical medical examinations.

The uterine cancers are largely classified into carcinoma colli and carcinoma corporis, which occur to different sites and different cells. Accordingly, in order to make an accurate diagnosis, it is necessary to sample only the required cells exactly from an aimed site.

Above all, in case of carcinoma corporis which initially occurs to the epithelial cells (cylindrical epithelial cells) of the nucous membrane on the surface of the endometrium, sampling of the cylindrical epithelial cells is essential for early therapy. Generally, the uterine cavity has a pear-like shape with a breadth inwardly increasing from the narrow cervix to present a flat oval shape in section, so that it is extremely difficult to sample the intended cells precisely from the endometrium without meticulous skill and experience. Besides, in consideration of the risk that the carcinoma corporis has possibilities of occurring in any part of the endometrium, the sample cells have to be taken uniformly from the entire regions of the endometrium although it is often found difficult because of the complicated shape of the uterine cavity.

In this connection, there have been introduced samplers of various types which are designed to take sample cells from the endometrium.

For instance, Japanese Laid-Open Utility Model Application 58-80208 discloses a sampler which is composed of a rod member having a cell sampling portion at the fore end thereof and slidably inserted in a flexible tube. After inserting the flexible tube into the uterine cervix, the rod is slide back and forth a number of times, scraping the endometrium with the cell sampling portion at the fore end of the rod to pick up sample cells thereon.

However, this sort of sampler employing a cell sampling portion of a simple rod-like shape is almost incapable of sampling cells uniformly from the entire endometrium in the uterine cavity which has a complicated shape as mentioned hereinbefore. Especially, difficulties are encountered in sampling cells from the endometrium in the fundus regions of the uterine cavity.

Japanese Laid-Open Patent Application 58-16891 discloses a sampler employing a handle member which has, at its fore end, a resilient helical portion which is formed by twisting a flat strip about the axis thereof. After insertion into the uterine cavity, the helical portion is turned to sample cells from uterine cavity walls. Similarly to the sampler of the above-mentioned Japanese Laid-Open Utility Model Application 58-80208, the helical sampling end portion which has a rod-like shape is incapable of sampling cells uniformly from all regions of the endometrium or from the fundus regions of the uterine cavity. In addition, sampled cells are apt to be squeezed into the grooves of the helical end portion together with unnecessary cells (i.e., cells other than cylindrical epithelial cells) which might lead to an inaccurate diagnosis.

SUMMARY OF THE INVENTION

It is therefore an object of the present invention to provide a uterine cell sampler which can collect sample cells from all regions of the endometrium in the uterine cavity in a safe and reliable manner.

In accordance with the present invention, the above-mentioned object is achieved by the provision of a uterine cell sampler which is characterized by a handle member slidably and rotatably inserted in a tube and a scraper portion in the form of a flexible loop formed at the fore end of the handle member and provided with scraper blades for scraping sample cells, the scraper loop being foldable and retractable into the tube upon sliding the handle member backward relative to the tube.

In use, prior to inserting the sampler, the scraper portion is folded into two halves overlapping one on the other and retracted into the tube by pulling the handle backward. After inserting the tube through the cervix, the handle member is propelled to push the scraping portion into the uterine cavity, whereupon the scraper portion spreads by resiliency into a loop which suitably inscribes the uterine cavity. As the handle is turned about its axis in this state to turn the flexible scraper loop in the uterine cavity, the loop is deformed in conformity with the shape of the uterine cavity to scrape the required sample cells from the endometrium as a whole with the scraper blades.

Succeedingly while the tube is in the inserted position, the handle is pulled backward to retract the scraper loop carrying the sampled cells into the tube in a folded state with the right and left halves of the loop straightened and folded one on the other. The sampler tube is withdrawn from the uterine cervix after the scraper loop has been completely retracted into the tube. It follows that the sampler can be extracted without permitting the sampled cells to fall off the scraper portion.

Preferably, the above-described scraper portion is formed of a looped scraper strip which has a sharp edge at least along one longitudinal side edge thereof to provide a scraper blade along the outer marginal edge of the loop. Where the right and left halves of the scraper loop are formed symmetrically relative to a bisecting center line, sample cells can be scraped and scooped by the edges of the right and left loop halves in a reliable manner while the scraping loop is turned about the axis of the handle member.

Further, it is preferable to provide spacer projections at least on the inner surface of one of the right and left loop halves to provide gap spaces between these loop halves when they are folded one on the other for retraction into the tube member, gripping sampled cells in the gap space securely without dropping the same. In a case where these spacer projections are provided with a scraping edge, sample cells can be scraped also by this edge when the sampler is moved back and forth.

Moreover, in order to make the scraping member easily deformable for the purpose of facilitating its retraction into and out of the tube, it is preferred to provide notches along one longitudinal side edge of the scraper strip.

To prevent the scraper strip from being retracted into the tube to an excessive degree, it is desirable to provide semi-spherical members at the boundaries between the right and left loop halves at the fore end of the scraper portion such that the semi-spherical members will form a ball of a diameter larger than the inside diameter of the tube and stop at the fore end of the tube when the loop halves are retracted in the flatly folded state. At the same time, the thus-formed ball serves as a cap for the tube, preventing cervical cells from creeping into the tube as the latter is passed through the uterine cervix. Further, where the semi-spherical members are provided with a scraper bade, they can scrape sample cells from fundus regions of the uterus in a secure manner.

Furthermore, the cell sampler of the invention, which employs a scraper portion in the form of a flexible loop, is extremely safe because the scraping loop is simply deformed when it is hit against the fundus by excessive insertion of the sampler into the uterine cavity, in contrast to conventional samplers with a sharp-pointed end which is very likely to hurt the fundus on such an occasion.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a partly cutaway front view of a cell sampler embodying the present invention;

FIG. 2 is a view similar to FIG. 1 but showing the sampler with the tube removed therefrom;

FIG. 9 is a sectional view of a sampler in another embodiment of the invention, taken in the same position as in FIG. 6;

FIG. 10 is a front view of a scraper portion in still another embodiment of the invention;

FIG. 11 is a front view of a scraper portion in a further embodiment of the invention; and FIG. 12 is an enlarged sectional view of the scraping member taken on line C—C of FIG. 11.

DESCRIPTION OF PREFERRED EMBODIMENTS

Figure 3:
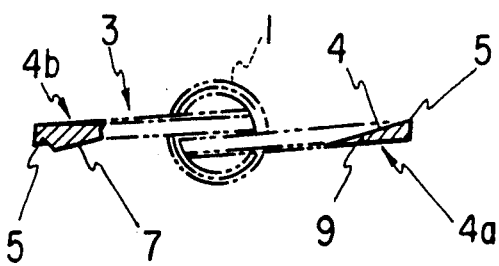
FIG. 3 is an enlarged sectional view taken on line A—A of FIG. 1.

Hereafter, the invention is described more particularly by way of the preferred embodiments shown in the drawings.

Referring first to FIG. 1, there is shown a first embodiment of the uterine cell sampler according to the invention, in which indicated at 1 is a flexible tube, and at 2 is a flexible handle which is slidably and rotatably inserted in the tube 1 and which is provided with a loop-like scraper portion 3 at its fore end. Preferably, the tube 1 and handle member 2 are formed of a synthetic resin material.

As clear from FIG. 2, the scraper portion 3 is formed by looping a scraper strip 4 which is provided by flattening part of the handle member 2, and retractably protrudable from the tube 1 by sliding the handle 2 relative to the latter. When protruded from the tube 1, the scraper portion 3 spreads by resiliency to take the form of a loop as shown in FIG. 1, and, when retracted into the tube 1, it is folded into halves which overlap one another as shown in FIG. 5.

Figure 4:
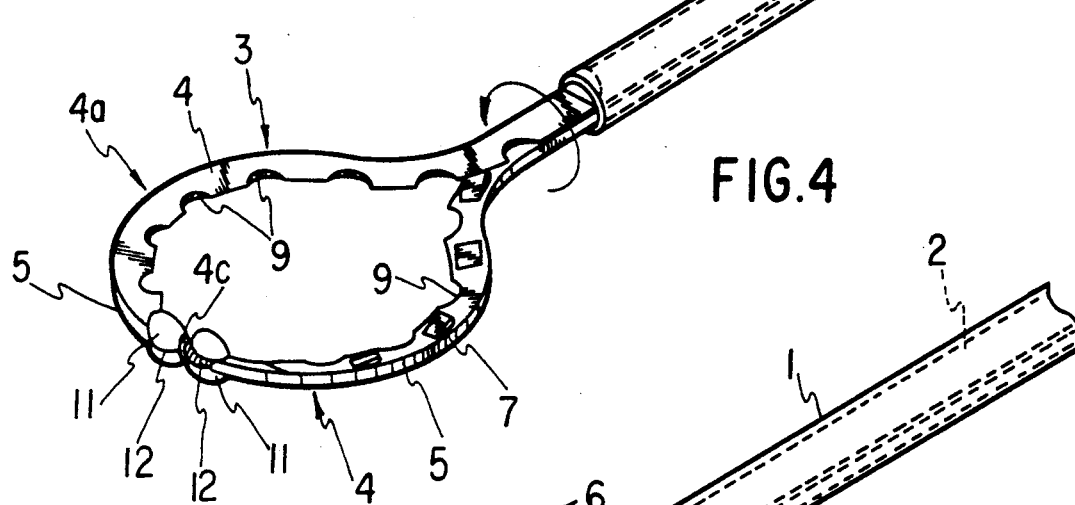
FIG. 4 is a perspective view of a scraper portion.
Figure 6:
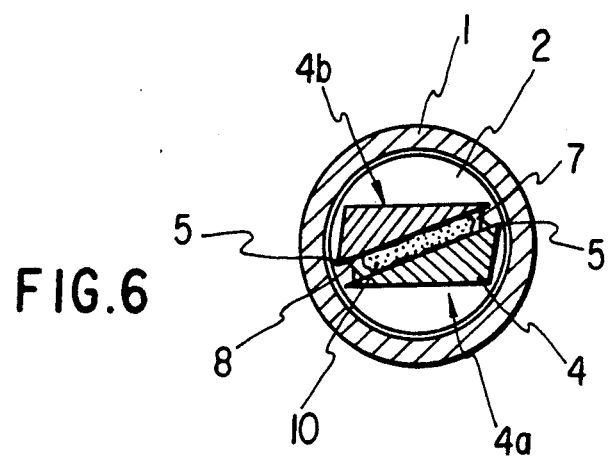
FIG. 6 is an enlarged sectional view taken on line B—B of FIG. 5.

As seen in FIGS. 3 and 4, the scraper strip 4 has a flat triangular shape in section, with a sharp edge along one longitudinal side edge thereof, to form a scraper blade 5 along the outer marginal edge of the scraper strip substantially parallel with the face of the right and left loop halves 4a and 4b which are curved in flat state and connected to each other by a flexible joint 4c. These right and left loop halves 4a and 4b are shaped symmetrically relative to a bisecting straight line through the center of the loop or to the axis of the handle member 2. Accordingly, as the scraper strip is turned after insertion into the uterine cavity, cylindrical epithelial cells of the endometrium are scraped off by the scraper blade 5 in a secure manner. Further, as the scraper portion 3 is retracted into the tube 1, the right and left loop halves 4a and 4b of the scraper strip 4 are folded one on the other in the form of a parallelogram (FIG. 6) for smooth retraction into the tube 1.

A plurality of sharp-edged projections 7 are provided at suitable intervals on the inner surface of at least one of the right and left halves 4a and 4b of the scraper strip 4. In addition for scraping off sample cells, these projections 7 form sample holding spaces 8 (see FIG. 6) between the scraper loop halves 4a and 4b as the latter are retracted into the tube 1 in the folded state, gripping sampled cells 10 in the spaces 8. Further, a plurality of notches 9 are provided at predetermined intervals along the scraper strip 4 on the side away from the scraper blade 5, for facilitating deformation of the scraper strip 4 into the spread loop form or into the closed or folded state at the time of protrusion or retraction into the tube 1. In the case where the above-mentioned projections 7 are provided on both of the scraper halves 4a and 4b, it is desirable to provide them in staggered or non-overlapping positions. The projections 7 are not restricted to the triangular shape shown in the drawings, and may be formed in other shapes if desired.

Figure 5:
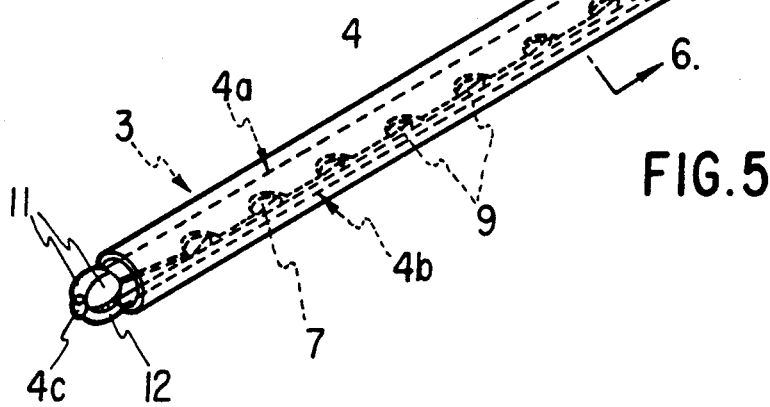
FIG. 5 is a perspective view of the scraper portion folded and retracted into the tube member.

Furthermore, provided at the boundaries between the right and left halves 4a and 4b of the scraper strip 4 at the fore end of the scraper portion 3 are semispherical members 11 which form a ball together when folded toward each other (FIG. 5). These semi-spherical members 11 are so dimensioned as to form a ball with a diameter greater than the inside diameter of the tube 1. Therefore, as the scraper portion 3 is retracted into the tube 1, the ball is stopped at the fore end of the tube 1 to thereby prevent over-retraction of the scraper portion 3 into the tube 1.

As seen in FIG. 4, a scraper blade 12 is formed at the top of each semispherical member 11 by forming a step with shifting a part of the semi-sphere so that the stepped blade 12 faces against the rotating direction of the scraper portion 3 for scraping sample cells. The scraper blades 12 permit obtaining sample cells from the uterine fundus in a more reliable manner. The height of the stepped portions which form the scraper blades 12 is preferably in the range of about 0.1–0.3 mm.

Leg portions 2a and 2b of the handle 2, contiguous to the opposite ends of the scraper strip 4, are formed in a semi-cylindrical shape as shown in FIG. 2, one leg portion 2a being provided with protuberances 14 which are engageable in locking holes 15 opposingly formed in the other leg portion 2b. The leg portions 2a and 2b are overlapped into a cylindrical form by fitting the protuberances 14 into the locking holes 15, and inserted into the tube 1 in this state.

It is preferable to provide a suitable reference mark 16 on the tube 1 for indicating the depth of insertion of the tube. It is also desirable to provide a stopper 17 or a mark on one side of the handle 2 to limit or indicate the maximum protrusion of the scraper portion 3.

Figure 7:
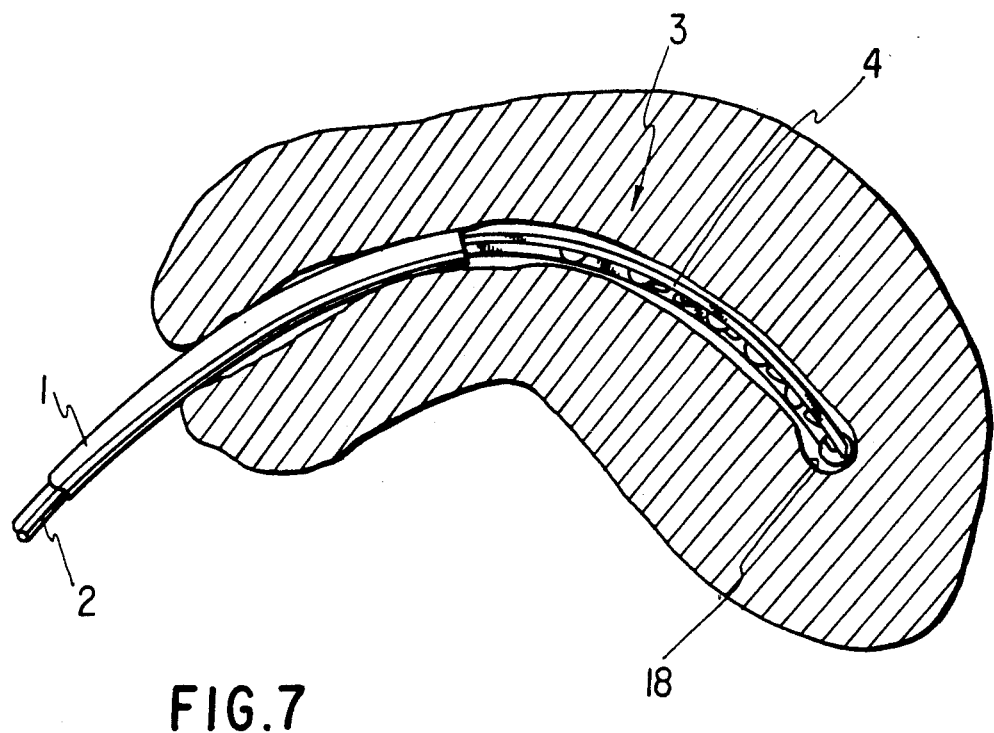
FIGS. 7 and 8 are sectional views of the sampler in use, taken from different directions.
Figure 8:
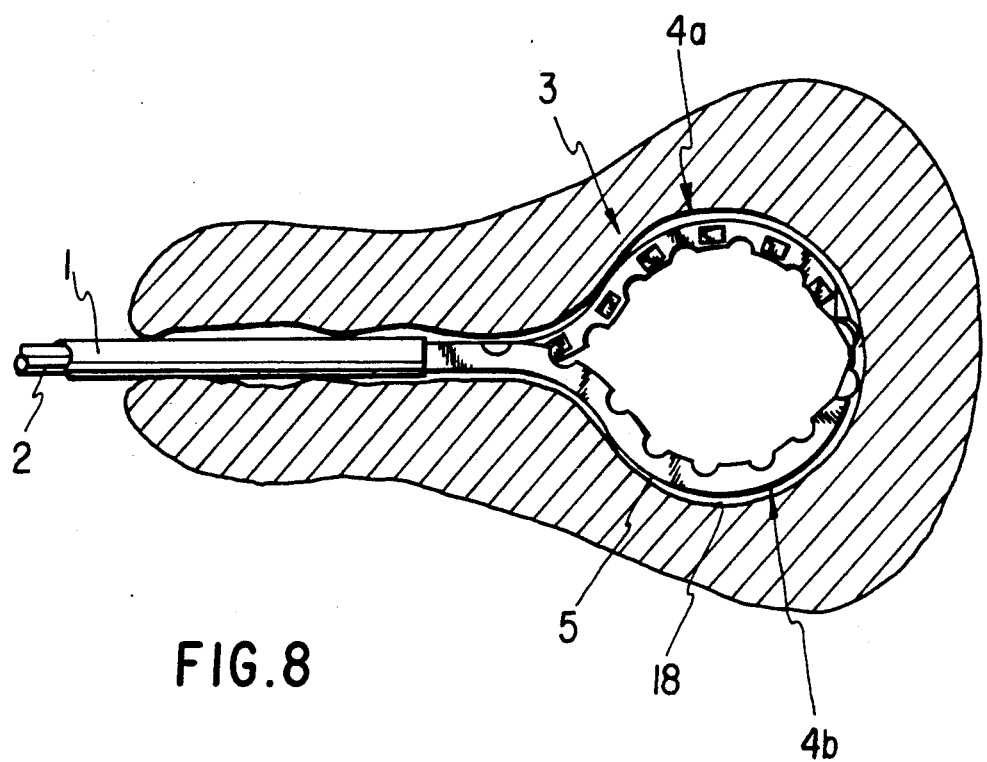

Prior to using the cell sampler of the above-described construction, the scraper portion 3 is retracted into the tube 1 to the position of FIG. 5 where the ball formed by the semispherical members 11 is stopped at the fore end of the tube 1. In this state, the tube is inserted to a suitable depth in the uterine cavity, and then the handle 2 is advanced as shown in FIGS. 7 and 8 to protrude the scraper portion 3 into the uterine cavity, whereupon the scraper strip 4 spreads by resiliency into the form of a loop which suitably inscribes the uterine cavity. By turning the handle 2 about its axis in this state, the flexible scraper strip 4 is turned in the uterine cavity, deforming its shape freely in conformity with the shape of the uterine cavity while scraping sample cells by the scraper blade 5 uniformly from the whole endometrium. Besides, sample cells can be scraped also by the edges of the projections 7 when the sampler is moved back and forth.

Then, upon retracting the handle 2 into the tube 1 which is still in the inserted position, the loop of the scraper strip 4 carrying the scraped sample cells is folded at the joint portion 4c into two halves 4a and 4b which are straightened and overlapped one on the other as they are retracted into the tube 1. The tube 1 is extracted as soon as the scraper portion 3 is completely withdrawn into the tube 1, thus taking out the sampled cells without permitting the same to fall off the sampler. At this time, the scraped sample cells are held in the spaces 8 which are formed between the folded right and left halves 4a and 4b of the scraper strip 4 by the projections 7 instead of being squeezed outside.

In addition to or in place of the scraper blade 5 which is provided along one side edge of the scraper strip 4, other scraper blades may be formed by providing other projections, grooves or stepped portions on the outer surfaces of the scraper strip 4.

Although the scraper strip 4 has been shown to have a triangular shape in section in the foregoing embodiment, it may be formed of other shapes, for example, in square shapes including a parallelogram and trapezoid or in crescent or semicylindrical shapes, and may be provided with the above-described projections 7 on both of its inner and outer surfaces. In this connection, FIG. 9 illustrates a second embodiment of the invention in which the projections 7 are formed on both sides of a scraper strip 4 of a trapezoidal shape. In a case where the projections 7 are formed on both sides of the scraper strip in this manner, a larger amount of cells are sampled as compared with a case where the projections are provided only on one side.

Illustrated in FIGS. 10 to 12 are further embodiments of the invention. FIG. 10 shows a third embodiment of the invention, in which the right and left halves 24a and 24b of a scraper strip 24 are connected to each other at the respective fore ends with a phase shift of 90 degrees in opposite directions from the loop face. FIGS. 11 and 12 show a fourth embodiment which employs a scraper portion 33 of a modified construction. Namely, the scraper portion 33 of the fourth embodiment employs a scraper strip which has a crescent shape in section and is provided with sharp-edged scraper blades 35 along both of its side edges along with a large number of saw-tooth-like scraper blades 36 which are formed in an inclined state on the outer surface of one of the halves of the scraper strip 34.

Accordingly, sample cells are scraped off by the scraper blades 35 at the side edges when the scraper portion 33 is turned and also by the scraper blades 36 on the outer surface when the scraper portion 33 is moved back and forth.

Needless to say, a large number of scraper blades 36 which are formed on the outer surface of one of the halves of the scraper strip 34 may be formed on the other half if desired.

The cell sampler of the invention is formed of a synthetic resin material as mentioned hereinbefore. Above all, it is preferred to be formed of a synthetic resin material which has excellent properties with regard to the cell deposition and transposition to slide glass, for example, of a polyolefinic resin such as polyethylene, polypropylene or a vinyl acetate copolymer, a polystyrene resin such as polystyrene or ABS, polyamide, an olefin-vinyl alcohol copolymer resin, a polyester elastomer or polybutylene terephthalate or a copolymer thereof.

What is claimed is:

1. A uterine cell sampler, which comprises:

a tube;

a handle member slidably and rotatably inserted in said tube, the handle member including a scraper portion in the shape of a flexible loop which is formed at the fore end of said handle member;

a scraper blade provide on said scraper portion for scraping sample cells from an endometrium, said scraper portion being protrudably retractable into said tube by sliding movement of said handle member relative to said tube, wherein said scraper portion includes a scraper strip of a flat band shape and having a sharp edge at least along one longitudinal side edge thereof; and right and left loop halves, said loop halves being spreadable into a loop by resiliency of said loop halves when said scraper portion protrudes out of said tube, said sharp edge on each of said loop halves facing outwardly of said loop substantially parallel to the plane of said loop when said scraper portion protrudes out of said tube so as to form a cell scraping edge wherein at least one of said loop halves includes a plurality of projections on an inner side portion thereof for forming a plurality of cell holding spaces between the two loop halves when said loop halves are positioned on one another in said tube upon retraction of said scraper portion into said tube.

2. A uterine cell sampler as defined in claim 1, wherein said projections each include a cell scraping edge.

3. A uterine cell sampler as defined in claim 1, wherein said scraper strip is provided with a series of notches along one side edge thereof to facilitate deformation of said scraper portion at the time of protrusion from or retraction into said tube.

4. A uterine cell sampler as defined in claim 1, further comprising semi-spherical members located at boundaries of the right and left loop halves meeting at the fore end of said scraper portion such that said semi-spherical members form a ball with a diameter larger than the inside diameter of said tube when said loop halves of said scraper strip are folded one on the other.

5. A uterine cell sampler as defined in claim 1, wherein said semi-spherical members include a scraper blade across respective top faces thereof for scraping sample cells.

* * * * *